United States Patent [19]

Waldmann

[11] 4,172,863

[45] Oct. 30, 1979

[54] HALOGEN-CONTAINING PHOSPHATES

[76] Inventor: John J. Waldmann, 220 E. Drewry La., Raleigh, N.C. 27609

[21] Appl. No.: 696,079

[22] Filed: Jun. 14, 1976

[51] Int. Cl.² ............................ C07F 9/09; C08K 5/52
[52] U.S. Cl. ..................................... 260/964; 548/111;
260/45.75 R; 260/45.75 K; 260/45.9 R;
260/45.95 D; 260/45.9 NP; 260/429 R;
260/429.5; 260/429.7; 260/429.9; 260/439 R;
260/446; 260/923; 260/932; 260/933; 260/937;
260/939; 260/941; 260/943; 260/945; 260/950;
260/953; 260/961; 260/963; 260/965; 260/968;
536/117
[58] Field of Search ................... 260/45.7 P, 953, 960,
260/963, 964, 429 R, 429.5, 429.7, 429.9, 439 R,
446, 965

[56] References Cited
PUBLICATIONS

DOS 2,254,062–Schnell, Jan. 17, 1974.

*Primary Examiner*—Anton H. Sutto
*Attorney, Agent, or Firm*—Cushman, Darby & Cushman

[57] ABSTRACT

Novel halogen-containing organic phosphorous compounds having the formula

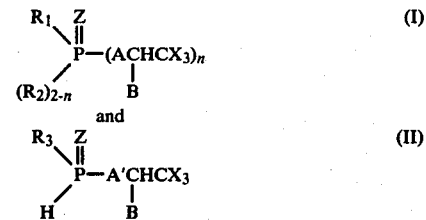

wherein
n is the whole number 1 or 2;
X represents chlorine or bromine;
Z represents oxygen or sulfur;
A represents a bivalent radical containing one or more oxy linkages;
A' represents a bivalent radical containing one or more oxy linkages or the direct P-C bond;
B represents a chloro, bromo, hydroxy, alkoxy, alkenyloxy, or ureidohydrocarbyl isocyanate radical;
$R_1$ repesents a chloro, bromo, hydroxy, hydrocarbyl or hydrocarbyl-oxy radical;
$R_2$ represents bromo, chloro, amino, hydrazino, hydroxy, —$R_1$, —OMe where Me is the salt of a metal selected from Na, K, Li, Zn, Mg, Ni, Ca, Ba, Sb, Ti, V, Sn, or —O—Q where Q represents an epoxy ester derivative of acrylic or methacrylic acid;
$R_1$ and $R_2$, together form an arylenedioxy radical when n is 1; and
$R_3$ represents a hydrocarbyl or hydrocarbyloxy radical.

These compounds are useful as reactive flame retardants in a number of synthetic and naturally occurring materials.

4 Claims, No Drawings

HALOGEN-CONTAINING PHOSPHATES

BACKGROUND OF THE INVENTION

This invention relates to novel halogen-containing organic phosphorous compounds having particular utility as flame retardants and as intermediates in the production of flame retardants. More particularly, this invention relates to a group of halogen-containing organic phosphorous compounds having reactive functionality and which are useful as reactive flame retardants and as intermediates in the production of reactive flame retardants for use in various materials. The invention also relates to synthetic and natural materials incorporating these flame retardant compounds.

The use of organic compounds containing phosphorous and halogen as flame retardant additives is well known. However, many of these flame retardant additives have been found unsatisfactory for one or more of the following reasons: (1) They must be incorporated in large amounts to be effective as a flame retardant; (2) They undesirably alter the chemical or physical properties of the material to which they are added; (3) They are not permanently retained in the material, but wash out or leach out over a period of time; (4) They are not thermally stable and split off chlorine, bromine, hydrogen chloride or hydrogen bromide when heated; and (5) They are toxic.

It is also known to employ as flame retardants, halogen-containing organic phosphorous compounds having reactive functional groups therein which permit the flame retardant to react with the material to which it is added to provide for better retention in the material. These known reactive flame retardant compounds reduce the problem of retention as compared to flame retardant additives, but generally still suffer many of the disadvantages mentioned above. Note, for example, U.S. Pat. No. 3,840,622 and the several patents relating to reactive flame retardants which are discussed therein by way of background. See also the following more recent U.S. Pat. Nos. 3,883,620; 3,886,237; 3,888,844, and 3,920,685.

In accordance with the present invntion, novel halogen-containing organic phosphorous compounds have been provided which overcome many of the problems above mentioned and are particularly useful as flame retardants and as intermediates in the production of flame retardants. These compounds exhibit exceptionally good flame retardant properties and thermal stability and contain reactive functional groups which allow them to readily combine chemically with the materials to which they are added.

SUMMARY OF THE INVENTION

The halogen-containing organic phosphorous compounds of this invention may be represented by the formula

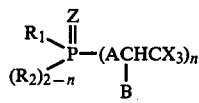   (I)

wherein
n is the whole number 1 or 2;
X represents chlorine or bromine;
Z represents oxygen or sulfur;
A represents a bivalent radical containing one or more oxy linkages;
B represents a chloro, bromo, hydroxy, alkoxy, alkenyloxy or ureidohydrocarbyl isocyanate radical;
$R_1$ represents a chloro, bromo, hydroxy, hydrocarbyl or hydrocarbyloxy radical;
$R_2$ represents bromo, chloro, amino, hydrazino, hydroxy, —$R_1$, —OMe where Me is the salt of a metal selected from Na, K, Li, Zn, Mg, Ni, Ca, Ba, Sb, Ti, V, Sn, or —O—Q where Q represents an epoxy ester derivative of acrylic or methacrylic acid; and
$R_1$ and $R_2$, when n is 1, may together form an arylenedioxy radical.

Compounds in accordance with the invention may also be represented by the formula

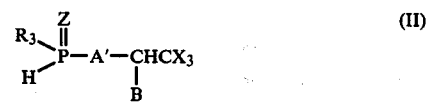   (II)

where B, X, and Z are as defined for Formula I, A' includes the linkages mentioned for A in Formula I as well as the direct P—C bond, and $R_3$ represents a hydrocarbyl or hydrocarbyl-oxy radical.

The present invention is also directed to fire retardant polymeric compositions containing a normally flammable polymer and a reactive flame retardant corresponding to Formula I or II.

DETAILED DESCRIPTION OF THE INVENTION

As defined above for Formula I, $R_1$ may represent a reactive functional group such as chloro, bromo, or hydroxy; or may represent a hydrocarbyl or hydrocarbyl-oxy radical. When $R_1$ in Formula I represents a hydrocarbyl or hydrocarbyl-oxy radical, such radical may be aliphatic, acyl, cycloaliphatic, aromatic, or heterocyclic, and may be substituted or unsubstituted. When $R_1$ represents an aliphatic radical, it may be a substituted or unsubstituted alkyl, alkenyl, or alkynyl which is optionally interrupted by one or more oxygen atoms. When substituted, the substituent is preferably a reactive one such as reactive chlorine or bromine, hydroxy, haloalkyl, amino, epxoy, etc.

The substituted or unsubstituted hydrocarbyl or hydrocarbyl-oxy radicals which $R_1$ may represent are illustrated by the following radicals:

—$OC_2H_5$; —$CH_3$; —$C_2H_5$; —$OCH_3$;
—$CH_2CH_2X$;

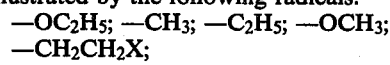

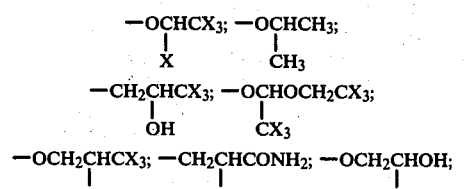

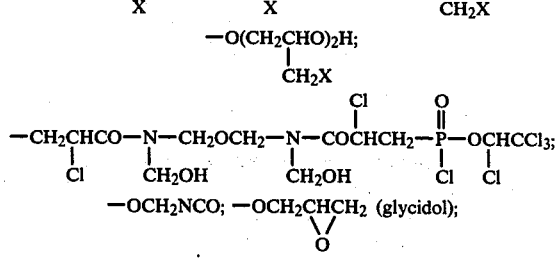

—$OCH_2NCO$; —$OCH_2CHCH_2$ (glycidol);
 \\/
  O

-continued

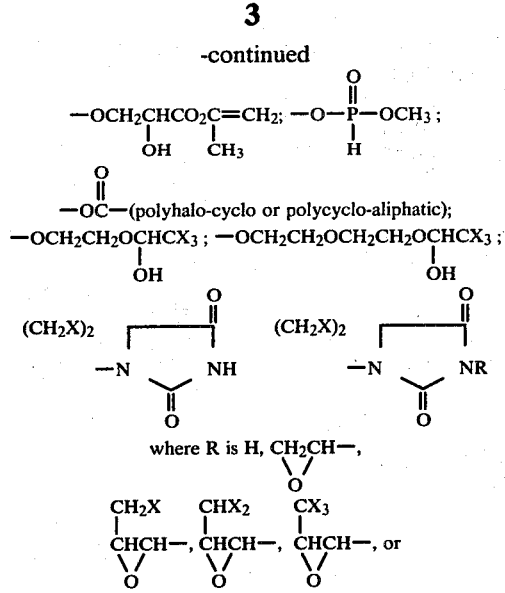

where R is H, CH₂CH—,
\\/
O

CH₂X   CHX₂   CX₃
|      |      |
CHCH—, CHCH—, CHCH—, or
\\/    \\/    \\/
O      O      O

—(CH₂)ₙ— (hydantoin derivatives, haloalkyl derivatives, haloaryl derivatives, alkylepoxy derivatives, aryl epoxy derivatives, unsaturated epoxy derivatives, and halocycloalkyl derivatives);

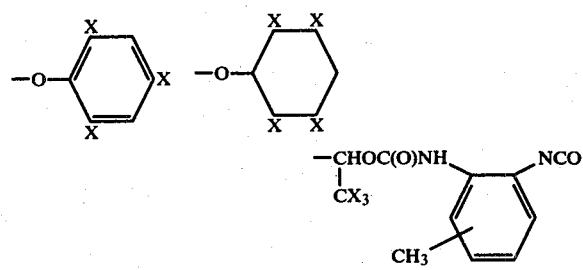

| —O—carbohydrate such as —O (glucosane); |
| —O—(Sucrose); |
| —O—(Fructose); —O—(Sorbitol) ; |
| —O—(Soforose); etc. |

In the foregoing radicals, X represents bromine or chlorine as defined for Formula I.

R₂ may represent a reactive phosphor-attached functional group such as bromo, chloro, amino, hydrazino, or hydroxy; or may represent an identical radical to the radical represented by R₁, R₂ may also represent —OMe, where Me is as defined for Formula I, such radical being produced by the reaction of a metal salt of the class described with a hydroxyl radical. R₂ may also represent —O—Q where Q represents an epoxy ester derivative of acrylic or methacrylic acid. The epoxy ester derivatives contemplated include the acrylic and methacrylic acid esters of: epoxy alkyl, epoxy alkenyl, epoxy cycloalkyl, epoxy aryl, and epoxy hetero cyclic compounds. As examples of such compounds may be mentioned glycidol acrylate and glycidol methacrylate.

When n=1 in Formula I, R₁ and R₂ may optionally join together as a divalent arylenedioxy radical, such as catechol.

A in Formula I is a bivalent radical containing one or more oxy linkages. Thus A may include the oxy radical (—O—) as well as bivalent radicals derived from an alkane which are interrupted by one or more oxygen atoms. When A is the latter, such radical may be substituted or unsubstituted. Such alkane would preferably contain from 1 to 6 carbon atoms. Radicals of this class would include the bivalent radicals of polyols such as ethylene glycol or diethlene glycol. Included in this class of bivalent radical are the following: oxy (—O—), alkyleneoxy (—RO—), oxyalkylene (—OR—), alkylenedioxy (—ORO—), oxydialkylene (—ROR—), (oxydialkylene) dioxy (—ORORO—), (aminodialkylene) dioxy, (—ORN(H)RO—), and (alkylaminodialkylene) dioxy (—ORN(R)RO—). R in the preceeding illustration represents an alkyl or alkylene radical. The following radicals, in particular, are contemplated:

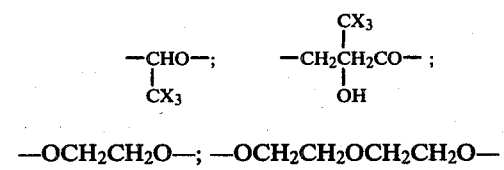

—OCH₂CH₂O—; —OCH₂CH₂OCH₂CH₂O—

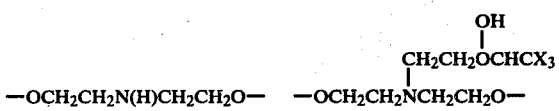

The radical represented by B is preferably a reactive one. Thus, B may represent a reactive halogen, preferably chloro or bromo, or a hydroxy radical. B may also represent an alkoxy or alkenyloxy radical. When B is an alkoxy or alkenyloxy radical, such radical is preferably substituted with one or more halogen atoms, especially chloro or bromo.

The following halogen-substituted alkoxy or alkenyloxy radicals, in particular, are contemplated for B:

—OCH₂CX₃; —OCH₂CHXCH₂X:

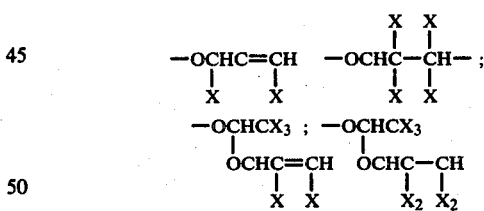

When B represents a uriedohydrocarbyl isocyanate radical, the hydrocarbyl moiety may be alkyl cycloalkyl, aryl, or polyaryl, an illustrative example of which is uriedotoluylisocyanate

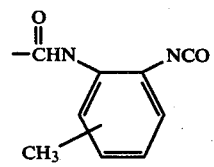

The compounds of this invention, as represented by Formulas I and II all include, as a characteristic feature thereof, the group

which appears at least once. This group is derived from chloral or bromal used as a material in producing the compound. This group provides for separation of the —CX₃ from the phosphorous atom, resulting in good heat and UV stability and good resistance to hydrolytic reaction.

The compounds of Formula I may be further defined according to structure. Thus, one class of compounds contemplated in accordance with Formula I may be more particularly represented by the formula

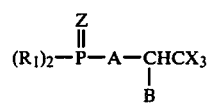

wherein A, B, R₁, X, and Z are as defined above for Formula I.

Especially useful are those compounds in accordance with Formula III wherein (i): A is —O—,

—OCH₂CH₂N(H)CH₂CH₂O—, or

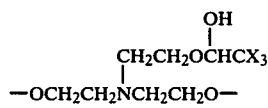

(ii): B is —Cl, —BR, —OH or —OCH₂CHXCH₂X
(iii): A is as defined in (i) and B is as defined in (ii).

Also particularly useful are those compounds in accordance with Formula III where R₁ comprises lower (C₁ to C₄) alkoxy and B is selected from hydroxy, chloro, and bromo.

Also contemplated are compounds in accordance with Formula III in which

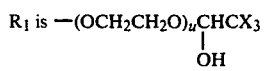  (u is 1 or 2)

and B is chlorine or bromine; or

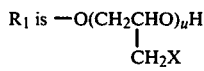  (u is 1 or 2)

and B is halogen-substituted alkoxy.

Very desirable, both as a reactive flame retardant itself and as an intermediate in the synthesis of other reactive flame retardants are the following tetrahaloalkyl phosphorodihalidate or phosphothiodihalidate compounds under Formula III:

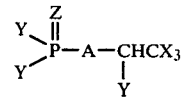

where A, X, and Z are as defined above for Formula I, and Y, independently of X, also represents chlorine and bromine. Also useful are the corresponding tetrahaloalkyl acids of Formula IV.

Also contemplated, and particularly useful as a flame retardant in urethanes, are compounds under Formula I wherein R₁=R₂=a uriedohydrocarby isocyanate derivative and B is a uriedohydrocarbyl radical.

Another class of compounds contemplated in accordance with the above Formula (I) may be more particularly represented by the formula

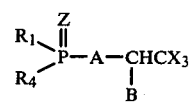

wherein A, B, R₁, X and Z are as defined in Formula I, and R₄ represents chloro, bromo, amino, hydrazino, hydroxy, —OMe, or OQ, where Me and Q are defined for Formula I.

Compounds of particular interest this class are those under Formula V in which A is oxy and B is chlorine or bromine. Another preferred class of compounds under Formula V are those where R₄ is selected from chloro, bromo, amino, hydrazino and hydroxy.

Still another class of compounds within Formula I may be more particularly represented by the formula

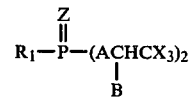

where A, B, R₁, X and Z are as defined above for Formula I.

Of particular interest are those compounds under Formula VI in which A is oxy or the bivalent radical of glycol or diethylene glycol.

Also within the present invention are halogen-containing organic phosphorous compounds in accordance with Formula II

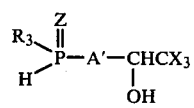

wherein X and Z are as defined for Formula I, A' represents the direct P—C bond or a bivalent radical containing one or more oxy linkages, and R₃ represents a hydrocarbyl or hydrocarbyloxy radical.

Preferred compounds of this class are phosphonic acids under Formula II where R₃ represents lower (C₁-C₄) alkoxy, and A' represents the direct P—C bond or a

linkage.

In the compounds of Formula I, the presence of at least one oxy linkage in the bivalent radical A gives very desirable heat and UV stability and resistance to hydrolytic reaction by providing for separation of the halogen from the phosphorous atom. These compounds exhibit stability and resistance to hydrolysis not found in organic phosphorous compounds of similar structure but where the chloral or bromal is attached directly to the phosphorous atom.

Monoalkyl phosphorous acid esters, however, when reacted with chloral or bromal to give the compounds of Formula II, result in products which have very acceptable resistance to heat, UV, and hydrolytic reaction, even though the chloral or bromal may be attached directly to the phosphorous atom.

The compounds of this invention are produced by various methods, all involving reacting chloral or bromal with certain organic and/or inorganic phosphorous compounds. The production of a number of the compounds of this invention, for example, involves reacting chloral or bromal with $PCl_5$ or $PBr_5$, which is then treated with water or sodium hydroxide or $H_2S$:

$$CX_3CHO + PY_5 \xrightarrow[\text{or } H_2S]{[NaOH/H_2O \text{ or triethylamine}/H_2O]} \text{(VIII)}$$

$$\xrightarrow{} \underset{Y}{\overset{Y}{\underset{|}{\searrow}}}\underset{Y}{\overset{O}{\overset{\|}{P}}}OCHCX_3$$

where X and Y are Br or Cl, Z is O or S.

This product (VIII) is used directly, or may be further reacted with various reactive compounds (which themselves may be derived from bromal or chloral) to produce other highly reactive polyhalogenated organic phosphorous compounds in accordance with this invention.

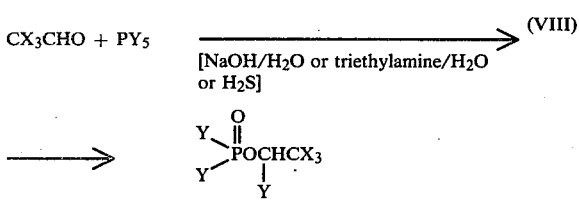

R* = a reactive functional product

Other compounds of this invention are produced by reacting chloral or bromal with mono or dialkyl phosphites, which in turn, may be further reacted with bromal or chloral, and/or with other reactive compounds, such as aryl diisocyanates for example.

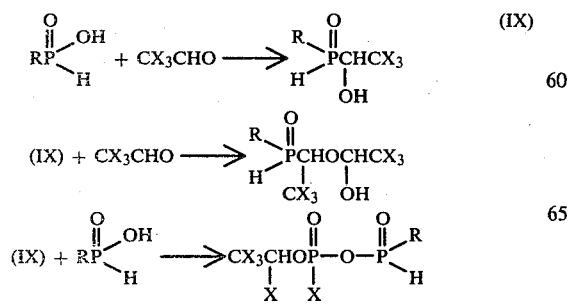

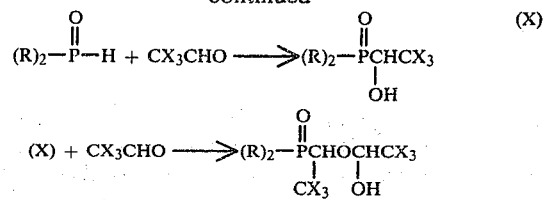

The compounds of the present invention exhibit exceptionally good flame retardant properties and thermal stability, and are particularly valuable as flame retardants for a variety of natural and synthetic polymeric materials including acrylics, polyacetals, polyurethanes, polyolefins, polycarbonates, ABS resins, polyesters, polyamides, woods, proteins, natural and synthetic cellulosic polymers, and rubber. The compounds may either be mixed with the material during polymerzation, or in the melt, or may be applied topically, as in the case of natural polymers or natural and synthetic textile fibers. The compounds may also be used with cellulosic fibers such as cotton and rayon and with natural silk or wool fibers.

The compounds are reactive and readily combine chemically with the materials to which they are added. They are further characterized by a relatively high ratio of phosphorous and halogen to alkylene linkages, to which at least in part, may be attributed the desirable flame retardancy and low toxicity properties, and the ability of the compounds to combine with the material without adversely affecting the physical properties thereof. The compounds are also characterized by being substantially neutral, i.e. no free acid.

The compounds of the present invention can be used in any proportion which is effective to provide the desired level of flame retardancy, and without adversely affecting the desired properties of the material to which they are added. Exact ranges vary depending upon the phosphorous and halogen content of the particular compound and the level of flame retardancy desired.

A more complete understanding of the compounds of this invention, and of methods of making and using them, will be obtained from the following examples, which are provided for purposes of illustration. It will be understood that the invention is not limited to these examples but that various modifications will be recognized by one of ordinary skill in the art.

Preparation of the Halogen-Containing Organic Phosphorous Compounds

EXAMPLE 1

Preparation of ββ β-trichloro-α-hydroxyethyl-β-ethoxy-phosphonate.

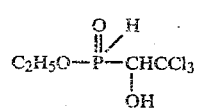

A three necked glass flask equipped with a reflux condenser open at the top, a mechanical stirrer, a thermometer, a cryostat-thermostat temperature control and dropping funnel with a drying tube to protect the reaction mixture from atmospheric moisture is charged with 1 Mole O-ethyl-hydroxyphosphite

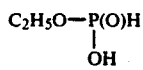

(prepared from diethyl-phosphate and sodium metal or hydroxide under reflux in an inert solvent).

The dropping funnel contains 1 Mole chloral. This is added slowly while maintaining the temperature of the reaction mass below 60° C. under a nitrogen blanket. The mixture is stirred an additional 20 minutes and maintained at 50° C.

The reaction mass is treated with an inert solvent at 35° C., and then purified. The product is analyzed as follows:

Calculated in the final product: Cl/P=3.44. Found by analysis: Cl/P=3.40.

EXAMPLE 2

Preparation of $\beta\beta\beta$-tribromo-$\alpha$-hydroxyethyl-$\beta$-ethoxyphosphonate.

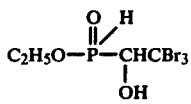

The procedure is similar to Example 1 except that 1.0 Mole bromal is used in place of chloral.

The product is analyzed as follows:

Calculated in the final product: Br/P=7.74. Found by analysis: Br/P=7.69.

EXAMPLE 3

Preparation of O,O-diethyl-$\alpha$-$\beta\beta\beta$-trichloroethylene-oxy-$\alpha'$-hydroxy-$\beta\beta\beta$-trichloroethylene-phosphonate

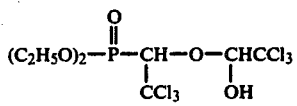

An apparatus similar to the one described in Example 1 is charged with 1 Mole of $\beta\beta\beta$-trichloro-$\alpha$-hydroxyethyl (or hydroxymethyl) phosphonic acid diethylester (material A), 150 ml of dioxane and 0.08% of a strongly acid cation exchange resin such as Ion Exchanger I, available from E. M. Laboratories, Inc. of Elmsford, N.Y. The percentage refers to parts by weight of material A. Material A is prepared by reacting diethyl phosphite with chloral following the procedure of Example 1. The dropping funnel contains 1 Mole chloral which is added slowly while maintaining the temperature of the reaction mass below 60° C., preferably at 50° C. A nitrogen blanket is used. The mixture is maintained an additional 20 min. at 50° C. after the exothermic reaction is complete. The product is cooled at room temperature, filtered and is purified by the same procedure as shown in Example 1. The product is analyzed as follows:

Calculated in the final product: Cl/P=6.87. Found by analysis=Cl/P=6.80.

EXAMPLE 4

Preparation of O-ethyl-$\alpha$-$\beta\beta\beta$-trichloroethylene-oxy-$\alpha'$-hydroxy-$\beta\beta\beta$-trichloroethylene-phosphonate.

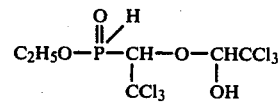

The procedure of Example 3 is followed, substituting material A with 1 Mole O-ethyl-$\beta\beta\beta$-trichloro-$\alpha$-hydroxy-ethylphosphonic acid.

The product is analyzed as follows:

Calculated in the final product: Cl/P=6.87. Found by analysis: Cl/P=6.80.

EXAMPLE 5

Preparation of O,O-diethyl-$\alpha$-$\beta\beta\beta$-tribromoethylene-oxy-$\alpha'$-hydroxy-$\beta\beta\beta$-tribromoethylene-phosphonate.

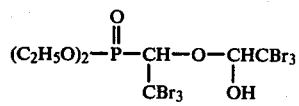

The procedure of Example 3 is repeated substituting 1 Mole bromal for the chloral used in that example.

The product is analyzed as follows:

Calculated in the final product: Br/P=15.48. Found by analysis: Br/P=15.39.

EXAMPLE 6

Preparation of tetrachloroethylene-phosphorodichloridate.

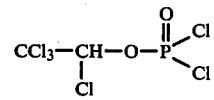

An apparatus similar to the one described in Example 1 is charged with an inert solvent of a low freezing point (300 mls) and 2.80 to 7 Moles preferably 3 Moles of PCl$_5$. The dropping funnel contains 0.97 to 2.40 Moles of chloral/or chloral hydrate, preferably 1 Mole which is added at such a rate that the reaction temperature is maintained below 40° C. The resulting mass is filtered to give tetrachloroethylene-phosphoro-tetrachloride:

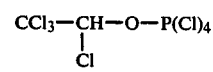

The resulting solution is cooled off to 5° C. to 0° C.

A concentrated solution of sodium hydroxide, 39 g in 39 g water, is added dropwise at such a rate that the temperature does not exceed 5° C. The additional time is 1.10 hours and the reaction mixture is stirred 20 to 40 minutes, preferably 30 minutes more at 12° to 25° C.

The reaction is illustrated by the equation:

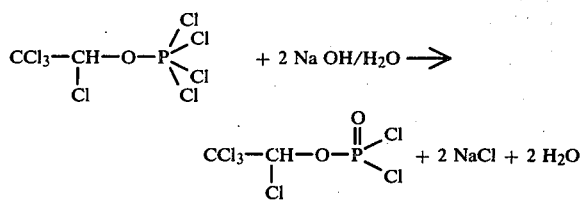

The salt is then filtered and the solution dried over Na₂SO₄. The drying agent is filtered out and washed with 45 ml methylenedichloride. The methylene dichloride is distilled out at atmospheric pressure resulting in almost total yield of tetrachloroethylene-phosphorodichloridate, a clear straw colored liquid:

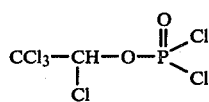

EXAMPLE 7

Preparation of tetrachloroethylene-phosphate-bis(-methoxyisocyanate).

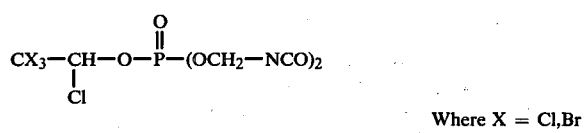

Where X = Cl,Br

Tetrachloroethylene-phosphorodichloride (Example 6) or tetrahaloethylene-chlorophosphate-α'-chloroethyl-phosphorodichloride (with the structure:

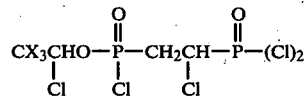

prepared from tetrachloroethylene-phosphorodichloride (Example 6) and vinyl phosphonic acid dichloride), 254 g and paraformaldehyde, 127 g are heated together to 30°-145° C. in an autoclave, preferably 138° C. for 160 minutes. After cooling and purification have been completed, the following products are the result:

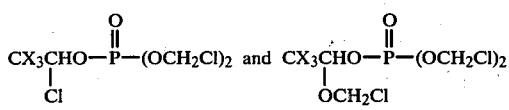

50.8 g of the tetrachloroethylene-bis(dichloromethyl)phosphate or trichloro ethylene-α-chloromethyl-bis(dichloromethyl)phosphate are added to 381 mls of dry benzene which contain 111.76 g of a Group I metal cyanate (such as sodium cyanate) at such a rate that the reaction temperature is maintained below 30°-35° C. The reaction mass is refluxed for 160 minutes and then cooled and filtered. The C₆H₆ is distilled off resulting in di- and triisocyanate phosphates.

Calculated in the final product: Cl/P=4.57. Found by analysis: Cl/P=4.33.

EXAMPLE 8

Preparation of tetrachloroethylene phosphothio dichloridate.

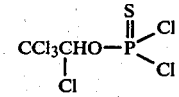

Example 6 is repeated substituting 2 Moles of H₂S for the 2 Moles of sodium hydroxide.

EXAMPLE 9

Preparation of tetrachloroethylene phosphoric acid or tetrachloroethylenethio phosphoric acid.

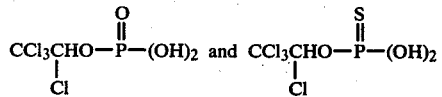

Examples 6 and 8 are repeated substituting 4 Moles of sodium hydroxide or 4 Moles of H₂S for the 2 Moles used in those examples.

EXAMPLE 10

Preparation of tetrabromoethylene phosphorodibromidate.

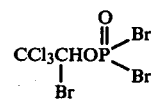

Example 6 is repeated substituting 1 Mole PBr₅ and 1 Mole bromal for the PCl₅ and chloral used in that example. The corresponding acid and thio derivatives are prepared following the procedures of Examples 8 and 9.

EXAMPLE 11

Preparation of βββ-trichloro-α-bromo-ethylene-phosphorodibromidate

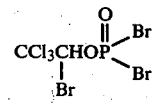

Example 6 is repeated using 1 Mole PBr₅ and 1 Mole chloral. The corresponding acid and thio derivatives are prepared following the procedure of Examples 8 and 9.

EXAMPLE 12

Preparation of 2.2'-bis(βββ-trichloroethylene-methoxy-βββ-trichloroethylene-α-oxy)-tetrachloroethylene-phosphate

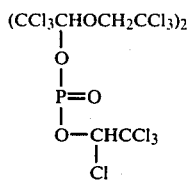

An apparatus similar to the one described in Example 1 is charged with 150 ml benzene and 1 Mole of βββ-trichloroethylene-α-hydroxy-α'-methoxy-βββ-trichloroethane (prepared from reacting chloral and 222-trichloroethanol). This mixture is cooled to about 10° C.

The dropping funnel contains 0.2 Mole of tetrachloroethylene-phosphorodichloridate (from Example 6), 50 ml benzene and 50 ml triethylamine; this is added slowly with stirring so as to maintain the temperature of the reaction-mass below room temperature.

After the addition, the solution is stirred for an additional 80 mintues at 20°-30° C. The benzene solution is washed to neutral, filtered, and the solvent is stripped under vacuum.

The resultant product is:

$C_{10}H_7Cl_{16}O_4P$

Calculated in the final product: Cl/P=18.31. Found by analysis: Cl/P=16.89.

EXAMPLE 13

Preparation of bis(βββ-trichloro-ethylene-methoxy-βββ-trichloroethylene-α-oxy)-2-chloroethyl-phosphonate

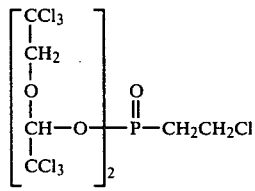

Procedure of Example 12 is used with 1 Mole of 2'-chloroethyl-phosphorodichloride replacing tetrachloroethylene-phosphorodichloridate.

The product is analyzed as follows:

$C_{10}H_{10}Cl_{13}O_5P$

Calculated in the final product: Cl/P=14.88. Found by analysis: Cl/P=14.82.

EXAMPLE 14

Preparation of tetrachloroethylene-bis(βββ-trichloroethylene-α-chloropropyl)-phosphonate.

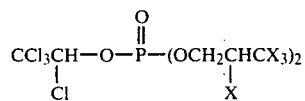

where X = Cl, Br where X=Cl, Br

An apparatus similar to the one described in Example 1 is charged with 250 ml of benzene, 0.65 Mole of tetrachloroethylene-phosphorodichloridate (Example 6) and 11.81 g anhydrous aluminum chloride.

The dropping funnel contains 2 Moles of βββ-trihalo-1,2-epoxy-alkyl (C₁ to C₆) or cycloalkyl such as βββ-trichloro-1,2-epoxy-propane. This is added slowly to the mixture at such a rate that the temperature of the reactants is maintained to about 50°-60° C. When the exothermic reaction ceases, heat is applied and the temperature is raised to 70° C. when 0.35 Mole of tetrachloroethylene phosphorodichloridate is added.

The product is purified by the procedure shown in Example 1. The solvent is stripped under vacuum at 60° C./12 mmHg.

The resulting product is:

$C_8H_7Cl_{12}O_4P$

Calculated in the final product: Cl/P=13.73. Found by analysis: Cl/P=13.68.

EXAMPLE 15

Preparation of 5,5-bis-(chloromethyl)-β-chloroethyl-1-hydantoin-phosphorochloridate.

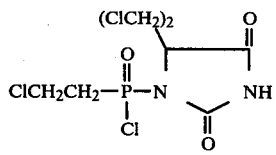

An apparatus similar to the one described in Example 1 is charged with 250 ml toluene, 1 Mole triethylamine and 2 Moles -5,5-bis(chloromethyl)-hydantoin (made from 1,3 dichloroacetone and sodium/or potassium cyanate).

The dropping funnel contains 0.65 α-chloroethyl-phosphoro-dichloride in minimal amount of toluene. This is added slowly to the mixture at such a rate that the internal temperature is maintained at about 55°-60° C. The procedure of Example 14 is followed. After filtration, the solvent is stripped under vacuum at 95° C./10 mmHg.

The resulting product is: $C_7H_9Cl_4N_2O_3P$

Calculated in the final product: Cl/P=4.58. Found by analysis: Cl/P=4.49.

EXAMPLE 16

Preparation of 5,5-bis-(chloromethyl)-α-tetrachloroethyleneoxy-α'-chloro-1-hydantoin-phosphonate.

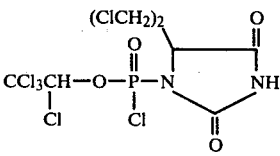

The procedure of Example 15 is repeated substituting α-chloroethyl-phosphorodichloridate with tetrachloroethylene-phosphorodichloridate (Example 6).

The resulting product is: $C_7H_6Cl_7N_2O_4P$

Calculated in the final product: Cl/P=8.01. Found by analysis: Cl/P=7.80.

EXAMPLE 17

Preparation of bis(-$\beta\beta\beta$-trichloroethylene-$\alpha$-hydroxy-$\beta$-oxy-$\beta\beta\beta$-trichloroethylene-$\alpha'$-hydroxy-bis(methyl)-1,2-pyrocatecholphosphate.

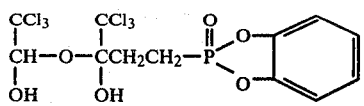

An apparatus similar to the one described in Example 1 is charged with 250 ml benzene, 100 ml triethylamine, 1 Mole -$\beta\beta\beta$-trichloroethylene-$\alpha$-hydroxy-$\beta$-oxy-$\alpha'$-hydroxy-trichloroethylene (made from reaction of chloral with chloral hydrate) and 5 g MgCl$_2$. The reactor is washed with N$_2$. Then 1 Mole 1-chloroethyl-1,2-pyrocatechol phosphate is added at room temperature at such a rate that the temperature of the reactants is maintained at about 55°–60° C. When the exothermic reaction ceases, heat is applied and the temperature is raised to 65° C. and kept for an additional 2 hours. The reaction mass is cooled to room temperature and filtered. The product is purified by the procedure shown in Example 1. The solvent is stripped under vacuum at 60° C./13 mmHg.

The resulting product is: C$_{12}$H$_{11}$Cl$_6$O$_6$P

Calculated in the final product: Cl/P=8.87. Found by analysis: Cl/P=8.82.

EXAMPLE 18

Preparation of (-$\beta\beta\beta$-tribromoethylene-$\alpha$-hydroxy-$\beta$-oxy-$\beta\beta\beta$-trichloroethylene-$\alpha'$-hydroxy-bis-(methyl)-1,2-pyrocatechol-phosphate.

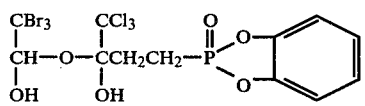

The procedure of Example 17 is repeated substituting -$\beta\beta\beta$-trichloroethylene-$\alpha$-hydroxy-$\beta$-oxy-$\alpha'$-hydroxy-trichloroethyene with 1 Mole of -$\beta\beta\beta$-tribromo-$\alpha$-hydroxy-$\beta$-oxy-$\alpha'$-hydroxy, $\beta\beta\beta$-trichloroethylene.

The product is analyzed as follows: C$_{12}$H$_{11}$Cl$_3$Br$_3$O$_6$P

Calculated in the final product: Br/P=7.74. Found by analysis: Br/P=7.71.

EXAMPLE 19

Preparation of bis($\beta\beta\beta$-trihalo-$\alpha$-hydroxyethylene-$\beta'$-oxy-diethyleneglycol-tetrachloroethylene phosphate.

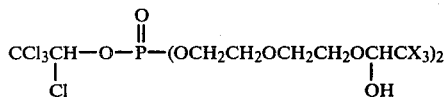

where X = Cl,Br where X=Cl, Br

The apparatus described in Example 1 is charged with 10 Moles tetrachloroethylene-phosphorodichloridate and 200 ml benzene. The dropping funnel contains 2 Moles of ($\beta\beta\beta$-tribromo-$\alpha$-hydroxyethane)-$\beta'$-oxy-2,2-oxydiethanol, 150 ml benzene and 210 g triethylamine is added at a temperature below 18° C. When the exothermic reaction ceases the solution is heated to 30° C. and kept for 30 min.

The salt is filtered and the resulting solution is heated under N$_2$ and purified by vacuum at 55° C., 18 mmHg.

The product is analyzed as follows:

C$_{14}$H$_{21}$Cl$_4$Br$_6$O$_{10}$P

Calculated in the final product: Br/P=15.48. Found by analysis: Br/P=15.38.

EXAMPLE 20

Preparation of -$\beta\beta\beta$-trihalo-$\alpha$-hydroxyethylene-$\beta'$-oxydiethyleneglycol-2-tetrachloroethylene-aminophosphate.

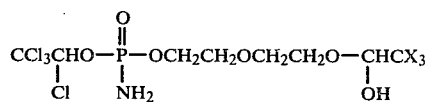

where X=Cl, Br

Into a solution of 0.1 Mole of -$\beta\beta\beta$-trichloro-$\alpha$-hydroxyethylene-$\beta'$-oxy-diethyleneglycol-2-tetrachloroethylene-chlorophosphate (prepared according to Example 19 but with the reactants in a ratio of 1:1) and 200 ml CCl$_4$, ammonia gas is passed while stirring at 20°–35° C. When an exothermic reaction is no longer observed the ammonia is stopped. The mass of the reaction is then treated, while stirring, with 80 ml of water to dissolve the by-product ammonium-chloride. The resulting mixture is stirred into chloroform, filtered and is distilled off at 50° C./12 mmHg to give:

C$_8$H$_{13}$Br$_3$Cl$_4$NO$_6$P

Calculated in the final product: Br/P=7.74. Found by analysis: Br/P=7.67.

EXAMPLE 21

Preparation of -$\beta\beta\beta$-trihalo-$\alpha$-hydroxyethylene-$\beta'$-oxy-diethyleneglycol-2-tetrachloroethylene-hydrazinophosphate.

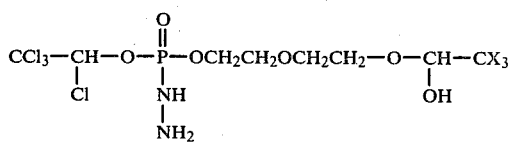

where X=Cl, Br

The procedure of Example 20 is repeated substituting the ammonia with 1 Mole of hydrazinehydrate.

After the purification the following product is obtained:

C$_8$H$_{14}$Cl$_7$N$_2$O$_6$P

Calculated in the final product: Cl/P=8.01. Found by analysis: Cl/P=7.92.

EXAMPLE 22

Preparation of $\alpha$-tetrachloro-ethylene-$\beta$-chloropropionamide-phosphorochloridate.

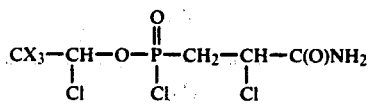

The apparatus described in Example 1 is charged with 1 Mole acrylamide or derivatives and 600 m. dioxane. The dropping funnel contains 1 Mole tetrachloroethylene-phosphorodichloride added slowly so that the temperature of the mixture remains below 30° C. The resulting mixture is stirred an additional 10 minutes at 30°–35° C. and 35–40 minutes at 45° C. The product is purified under $N_2$ by vacuum at 45° C./15 mmHg.

The product is analyzed as follows:

$C_5H_6Cl_6NO_3P$

Calculated in the final: Cl/P=6.86. Found by analysis: Cl/P=6.82.

EXAMPLE 23

Preparation of poly(halo-propane) -α-oxy-βββ-trihaloethylene-α'bis(β'-halo-methyl-propanol)-phosphate.

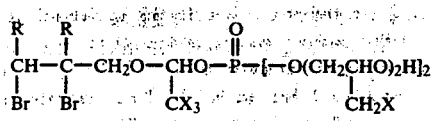

where
R=H,Br
X=Cl,Br

An apparatus described in Example 1 is charged with 1 Mole α,β-dibromo-propanol/or α,α',β,β'-tetrabromo-propanol under $N_2$. The temperature is raised to 45°–55° C. when 1 Mole bromal/or chloral is added slowly. The resulting mass reaction is cooled below 10° C. when 1 Mole of $P_2O_5$ is added, keeping the temperature of the solution below 15° C. After the exothermic reaction has ceased heat is applied to 45°–50° C. when over 4 Moles epichlorohydrin/or epibromohydrin are added slowly. The temperature is maintained below 70° C. The solution is purified and cooled at room temperature.

The product is identified as: $C_{17}H_{27}Cl_7Br_2O_9P$

Calculated in the final product: Br/P=5.16. Found by analysis: Br/P=5.10.

EXAMPLE 24

Preparation of bis (2,3-dibromo-2-propene-1-oxy-βββ-tribromo-ethylene-α-oxy)-phosphate-bis (β-chloromethyl-propaneglycol).

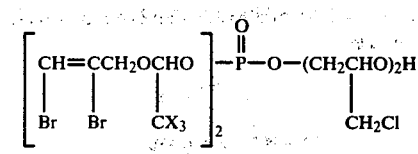

The procedure of Example 23 is repeated in presence of 2,3-dibromo-2-propene-1-oxy-βββ-tribromo-α-hydroxyethylene.

The product is analyzed as follows:

$C_{16}H_{19}Cl_2Br_{10}O_8P$

Calculated in the final product: Br/P=25.88. Found by analysis: Br/P=25.79.

EXAMPLE 25

Preparation of bis (βββ-trichloroethylene-1,1'-carboxyaminophenyl-isocyanate)phosphono-2-oxy-βββ-trichloroethylene-α-carboxyaminophenyl-isocyanate

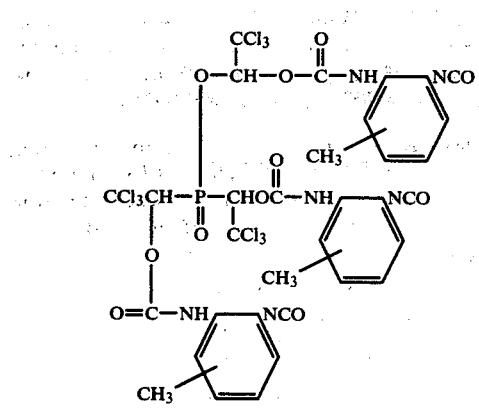

An apparatus similar to the one described in Example 1 is charged with 1 Mole bis-(βββ-trichloroethylene-1,1'-hydroxy)phosphono-oxy-α-hydroxy-βββ-trichloroethylene (prepared by reacting bromal or chloral, or chloral hydrate with Me(I,II,III)(phosphide), such as

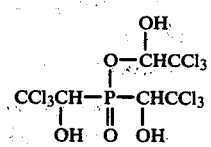

The dropping funnel contains 3 Moles alkyl or aryl or polyaryl-diisocyanate, such as toluene diisocyanate (80/20); this is added slowly while maintaining the temperature of the reaction mass below 80° C. under the nitrogen blanket. The mixture is maintained and stirred an additional 90 minutes.

5.58 Moles of additional toluene diisocyanates with 25% NCO groups (prepared by heating TDI or other aryl polyisocyanates with lithium acetate) are added. The product is a pale yellow liquid containing the structure as follows:

$C_{33}H_{24}Cl_9N_6O_{11}P$

Calculated in the final product: Cl/P=10.30. Found by analysis: Cl/P=10.26.

EXAMPLE 26

Preparation of βββ-trichloropropane-α-carboxyaminoisocyanate-phosphono-bis(trichloroethylene-oxy-α'-carboxy-aminoisocyanate).

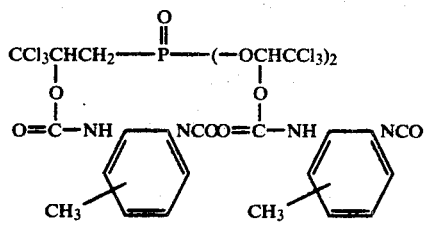

The procedure of Example 25 is followed substituting the material with bis($\alpha$-hydroxy-$\beta\beta\beta$-trichloroethylene)-phosphono-$\beta\beta\beta$-trichloro-$\alpha$-hydroxy-propane (made from $\alpha$-hydroxy-methyl-phosphonic acid

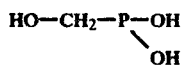

and chloral)

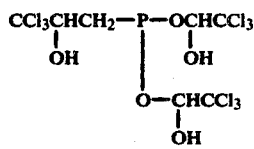

The resulting product is a pale yellow liquid containing the structure as follows: $C_{34}H_{26}Cl_9N_6O_{11}P$ Calculated in the final product: Cl/P=10.30. Found by analysis: Cl/P=9.90.

EXAMPLE 27

Preparation of 1-bis($\beta\beta\beta$-trihaloethylene-$\alpha$-urylenephenyl-isocyanate) oxy-diethyleneglycol-2-tetrachloroethylenephosphate

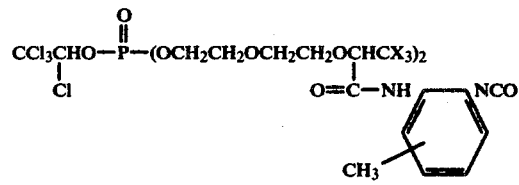

The apparatus described in Example 1 is charged with 1 Mole tetrachloroethylene phosphorodichloridate (Example 6) and 2 Mole of diethylene glycol under the nitrogen blanket. The temperature of the mixture is raised to 50° C. and 2 Mole of triethylamine is added. After purification the resulting solution is treated with 2 Mole of chloral at 50° C. and is maintained for 40 minutes. 2 Mole of toluene diisocyanate with 25% NCO groups is added at 90° C. where it is maintained an additional 25 to 35 minutes. The product is pale yellow liquid containing the structure

Calculated in the final product: Cl/P=11.44. Found by analysis: Cl/P=11.36.

EXAMPLE 28

Preparation of $\alpha$-tetrahalo-ethylene-$\alpha'$-polyhalo phenyl-Me-phosphate and $\alpha$-tetrahalo-ethylene-$\alpha'$-polyhalo cycloalkyl-Me-phosphate.

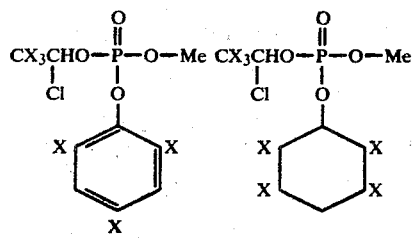

Where:
X=Cl, Br
Me=Na, K, Li, Zn, Mg, Ni, Ca, Ba, Sb, Ti, V, Sn salts

An apparatus similar to the one described in Example 1 is charged with 0.2 Mole of tetrachloroethylene-phosphorodichloridate or phosphorothiochloridate (Examples 6 and 8) and 0.2 Mole of polyhalo cycloalkyl or polyhalo aryl-alcohol, such as 2,4 6-tribromophenol and 100 ml of dried benzene. The dropping funnel contains 0.2 Mol triethylamine and is added at such a rate that the temperature never exceeds 25° C.-30° C. The mixture is stirred for 2 hrs. at 50° C. The reaction mass is filtered and washed with benzene. The resulting solution is warmed at 40°-50° C. in presence of triethylamine when is added 18 g H$_2$O in 12 minutes after purification, resulting in:

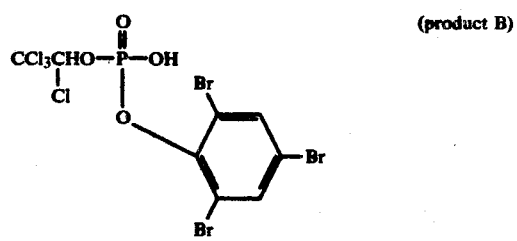

(product B)

To the resulting solution is added 0.5 g potassium salt and heated to 50° C. for 20 minutes.

The unreacted product is distilled off to give:

Calculated in the final product: Br/P=7.74. Found by analysis: Br/P=7.64.

EXAMPLE 29

Preparation of $\alpha$-tetrahalo-ethylene-$\alpha'$-phosphato-(metha) acrylate:

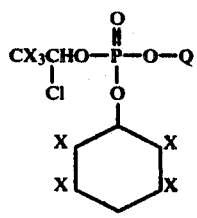

where
X=Cl, Br
Q=H, or (alkyl, alkenyl, cycloalkyl, aryl and heterocyclic) epoxy ester derivatives of acrylic and methacrylic acid The procedure of Example 28 is repeated substituting tetrachloro cyclohexanol for 2,4,6-tribromophenol and substituting the metal salts with 1 Mole of appropriate epoxyacrylate or methacrylate derivatives (such as cycloalkyl/or aryl/or heterocyclic such as hydantoins derivatives).

The structure shown below specifically illustrates the reaction with 1 Mole of glycidolmethacrylate at 50° C. in presence of TMAC as catalyst and heated for 10 to 120 minutes at 60° C. The unreacted product is distilled off to give:

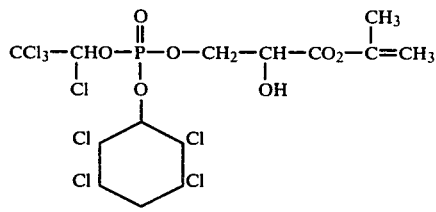

Calculated in the final product: Cl/P=9.15. Found by analysis: Cl/P=9.09.

EXAMPLE 30

Preparation of α-tetra-halo-ethylene-α'-bis(-polyhalocyclohexane) phosphate

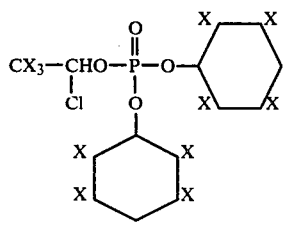

Where
X=Cl,Br

An apparatus similar to the one described in Example 1 is charged with 0.2 Mole of tetrachloro-ethylene-phosphoro dichloride (Example 6) or phosphorothiochloridate (Example 8) and 0.4 Mole of polyhalo-cyclohexanol such as tetrachlorocyclohexanol (or isomers) or polyhalo-aryl-alcohol and 100 ml of dried benzene under N$_2$. The dropping funnel contains 0.6 Mole triethylamine and is added at such a rate that the temperature never exceeds 25°-30° C. The mixture is stirred for 2 hrs at 50° C. under N$_2$. The product is purified following the same procedure as in example.

The product is analyzed as follows: C$_{14}$H$_{13}$Cl$_{12}$O$_4$P

Calculated in the final product: Cl/P=6.87. Found by analysis: Cl/P=6.80.

EXAMPLE 31

Preparation of poly(halo-hydroxy-phosphato)-carbohydrate.

The apparatus described in Example 1 is charged with 41.13 grams carbohydrate (sucrose, fructose, glucose, sorbitol, soforose) such as glucosane, 165 ml dioxane and 40 grams triethylamine. The mixture is warmed at 65° C. under N$_2$ and then 52 grams of tetrachloro-ethylene-phosphoro dichloride is added and maintained 1½ hr at this temperature. The reaction mass is cooled to room temperature and filtered. The resulting product contains the following structure:

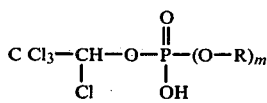

where R is the radical polymer carbohydrate. The reaction mass is heated to 50° C. for 20 minutes and 171 grams epichlorhydrin is added at such a rate that the temperature never exceeds 80°-90° C. The resulting solution is heated at 80°-90° C. for additional 360 minutes. The unreacted compounds are recovered at 80° C./8 mm to give a viscous polymeric material.

C$_{30}$H$_{36}$Cl$_{18}$O$_{18}$P$_3$

Calculated in the final product: Cl/P=6.87. Found by analysis: Cl/P=6.77.

EXAMPLE 32

Preparation of bis-(βββ-trihalo-α-hydroxyethylene-oxy-ethaneaminoethoxy-2-bis(polyhalo-propane)-phosphate.

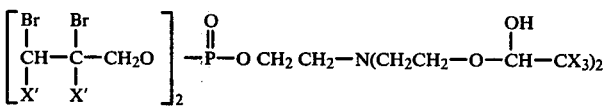

Where
X=Cl,Br
X'=H,Br

An apparatus described in Example I is charged with 0.37 Mole of triethanol amine in 100 ml of 1,1-dichloro-ethylene and 102 g triethylamine. 0.123 Mole bis (α,β-dibromo-propane)-phosphorochloridate /or bis (α,α',β,β'-tetrabromo-propane)-phsophoro-chloridate is placed in the dropping funnel with 50 ml 1,1-dichloro-ethylene. This solution is added slowly to the mixture in the reactor so that the reaction temperature does not rise above 15° C.-20° C. The reaction mixture is allowed to warm at room temperature for about 10 hours. The solution is evaporated in a vacuum to yield a viscous oil residue which is then dried over Na$_2$So$_4$ (if necessary) and filtered. The resultant materials are represented by the chemical formula:

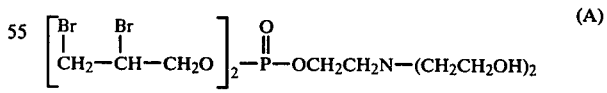
(A)

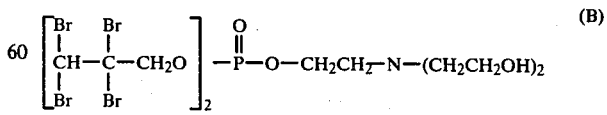
(B)

A neutral sample 1 Mole (product A or B) as prepared above is heated to 40°-45° C. under a nitrogen blanket. The dropping funnel contains 2 Moles of chloral/or bromal/or βββ-trihalo-1,2-epoxypropane (Chloral is used to obtain the structure illustrated above).

This solution is added slowly over a period of 30–40 minutes to the reactor. When the exothermic reaction ceases, the mass is warmed at 50°–60° C. for 80 minutes.

The product is identified as the structure above.

Calculated in the final product: Br/P=10.32 (A); Br/P=20.64 (B). Found by analysis: Br/P=10.28 (A); Br/P=20.61 (B).

EXAMPLE 33

Preparation of bis(tetrachloroethylene-phosphorochloride-β-chloropropyon-α-hydroxymethyl-β-methoxy-imine)

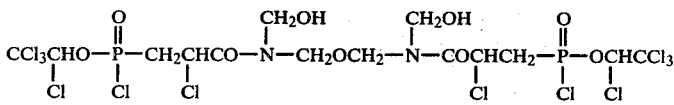

An apparatus described in Example 1 is charged with 2 Moles of tetrachloroethylene-phosphoro chloroide-β-chloropropyonamide, 100 g dioxane and 15.75 g p-toluene sulfonic acid and heated at 40° C. The dropping funnel is charged with 4.75 Moles of formaldehyde. The solution is added slowly while maintaining the temperature of the solution below 65° C. The resulting mixture is stirred an additional 80 minutes at 65° C. and then it is cooled to room temperature. The product is purified following the same procedure as in Example 1.

The product is analyzed as follows:

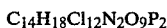

Calculated in the final product: Cl/P=6.87. Found by analysis: Cl/P=6.79.

EXAMPLE 34

Tetrahaloethylene-β-chlorophosphate-β'-hydrogenoxymethylphosphite:

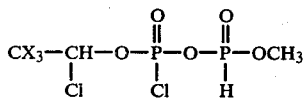

Where X=Cl, Br

An apparatus similar to the one described in Example 1 is charged with 0.1 Mole of tetrachloroethylene-phosphorodichloride (Example 6) or tetrachloroethylene-phospho thiodi-chloride (Example 8), 102 mls of triethylamine and 100 mls of inert solvent. The dropping funnel contains 0.1 Mole of monoalkyl /or cycloalkyl /or aryl hydrogen phosphite such as β-oxymethylhydrogen-phosphite.

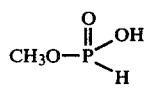

and is added at such a rate that the temperature never exceeds 10° C. The mixture is stirred 30 minutes at room temperature and then gently heated to the boiling point of the solvent for 20–120 minutes, preferably 40 minutes. The product is filtered and the solvent distilled off.

The product is analyzed as follows: $C_3H_5Cl_5O_5P_2$

Calculated in the final product: Cl/P=2.86. Found by analysis: Cl/P=2.77.

EXAMPLE 35

Preparation of tetrahaloethylene-β-chlorophosphate-1,4,5,6,7,7-hexachlorobicyclo-(2,2,1)-5-heptane-2,3-carboxy-β'-cyclohexanol.

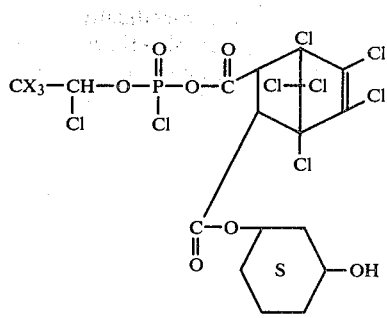

An apparatus similar to the one described in Example 1 is charged with 1 Mole of 1,4,5,6,7,7-hexachlorobicyclo-(2,2,1)-5-heptane-2,3-acid anhydride, 200 mls benzene and 1 ml (n-benzyldiemethylamine. This is mixed at 45°–55° C. preferably 45° C. under $N_2$ until dissolved. Then 1 Mole (+10% excess) of cyclohexene oxide is added dropwise within 40–60 minutes at the same temperature.

102 g of triethylamine is slowly added. The dropping funnel contains 1 Mole tetrachloroethylene-phosphorodichloride (Example 6). [Tetrahaloethylene-β-chlorophosphate-α'-chloroethyl-phosphoro-dichloride (Example 7), or tetrahaloethylenephosphor thiodichloride (Example 8) may be used instead.] This is added at such a rate that the temperature never exceeds 5° to 15° C. preferably 10° C.

The mixture is stirred 30 to 80 minutes, preferably 30 minutes, and then gently heated to the boiling point of the solvent for 20–120 minutes, preferably 40 minutes. The product is filtered and concentrated.

The product is analyzed as follows:

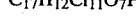

Calculated in the final product: Cl/P=12.59. Found by analysis: Cl/P=12.47.

INCORPORATION OF THE COMPOUNDS IN RESINS AND OTHER MATERIALS

EXAMPLE 36

Thermoplastic-Thermoset Acrylic. A suitable reaction vessel equipped with stirrer, temperature control, condenser and dropping funnel with a drying tube is charged with:

| | |
|---|---|
| pyrophosphoric acid, such as chloropyrophosphoric acid $Cl(OH)(O)POP(O)(OH)_2$ | 21.84 pbw |
| urea (or urea derivatives) | 58.84 pbw |

The mixture is heated to 50° C. for 20 min. to 2 hours and then cooled to room temperature and 8 pbw urea and 18 pbw FR of Example 4 is added. The dropping funnel contains acrylic alkyl ester or metha (acrylic) alkyl-ester such as methylmethacrylate 50.80 pbw and vinylnitrile derivatives such as acrylonitrile 127 pbw. These are added and stirred until the solution becomes almost clear.

The resulting solution could be polymerized by UV, electron beam or redox system.

To the above solution is added 1% pbw of organic peroxide such as 2,4-dichlorobenzoylperoxide and N,N-di(2-hydroxyethyl)-p-toluidine. The solution is allowed to heat at 40° C. under $N_2$ until it becomes very viscous and the reaction appears to be practically complete. The bulk casting is then baked several hours at about 70° C. to assure complete polymerization, resulting in a thermoplastic fire resistant product. If the product is heated until 200° C. for 35–40 minutes the acrylic copolymer becomes thermoset and fire resistant.

EXAMPLE 37

The procedure of Example 36 is repeated in presence of vinylamide derivatives such as acrylamide 25.40 pbw and metal oxalic complex such as $K_2[T_iO(C_2O_4)_2]2H_2O$ The resulting (co)polymer is a fire resistant product.

EXAMPLE 38

The procedure of Example 36 is repeated in presence of:

| methacrylic acid | 58.42 pbw |
|---|---|
| methacrylonitrile | 68.58 pbw |
| urea | 8.89 pbw |
| 4-amino-2,5-imino-amido-s-triazine | 0.8 pbw |
| α-tetrachloroethylene--β-chloropropionamide-phosphorochloridate (Example 22) | 15 pbw |
| AIZBN initiator (azoisobutyronitrile sold under the trade name VIZO by DuPont) | 0.8 pbw |

These materials are heated 48 hours at 50° C. under $N_2$ and then 4–10 minutes at 90° C. The resulting moldable thermoplastic (co) polymer is fire resistant.

EXAMPLE 39

In a suitable apparatus described in Example 36 is charged with methylmethacrylate monomer and/or other acrylic or vinyl monomers (as described composition in U.S. Pat. Nos. 3,847,865; 3,843,612; 2,750,320 and 2,367,661) such as:

| methylmethacrylate | 49 | pbw |
|---|---|---|
| methacrylic acid | 21 | pbw |
| 3,4-epoxycyclohexylcarbinyl-3.4-epoxycyclohexanecarboxylate | 29.4 | pbw |
| 2(2' - hydroxy-50' -methyl-phenyl)benzotriazole | 0.1 | pbw |
| 0.4-NaOH | 0.4 | pbw |
| 75% solution of t-butylperoxy-pivalate | 2 | pbw |
| O-ethyl-α-βββ-trichloroethylene-oxy-α'-hydroxy-βββ-trichloroethylene phosphonate (as described in Example 4) | 17 | pbw |
| hydrafobe silica | 6% | pbw in MMA basis |
| ZnCl₂ | 0.1% | pbw in MMA basis |

The procedure is carried out the same way as described in U.S. Pat. No. 3,843,612. The resulting polymer is fire resistant.

EXAMPLE 40

In a suitable apparatus described in Example 36 is charged one of the compsitions as described in U.S. Pat. No. 3,843,594, such as:

| methylmethacrylate | 435 | pbw |
|---|---|---|
| glycidol methacrylate | 266 | pbw |
| methacrylonitrile | 159 | pbw |
| hydrofobe silica | 0.8% | pbw of MMA |
| 5,5-bis(chloromethyl)-α-oxy-tetrachloroethylene-α'-chloro-1-hydantoin phosphonate (Example 16) | 20 | pbw |
| βββ-trichloro-α-hydroxyethyl-β-ethoxy-phosphonate (Example 1) | 5 | pbw |
| MoO₃-Cu₂O | 5% | pbw of MMA |

The resulting thermoset molding powder is fire resistant.

EXAMPLE 41

In a suitable apparatus described in Example 36 is charged with one of the compositions described in U.S. Pat. Nos. 3,033,813; 3,104,154 or 3,736,241, such as:

To 100 g of a 50% aq. $ZnCl_2$ there are added 5 g homopolymeric acrylonitrile and 1 g polypyrolidone (following the procedure of U.S. Pat. No. 3,033,813), and bis(2,3-dibromo-2-propene-1-oxy-βββ-tribromoethylene-α-oxy)-phosphate-bis (β-chloromethyl-propaneglycol) as described in Example 24. The resulting acrylic fiber is fire resistant.

EXAMPLE 42

The following mixture:

| polypropylene powder (Melt index 10) | 90 | pbw |
|---|---|---|
| α-tetrachloroethylene bis(α'-polychloro cyclohexane)-phosphate (Example 30) | 10 | pbw |
| bis-(β-chloromethyl)-vinyl phosphate-Zn (salt) | 0.5% | pbw of PP |
| UV Stabilizer Tinuvin P (Ciba-Geigy) | 0.08% | pbw of PP | is made homogeneous by tumbling. A sample is rolled between 100°–135° C. and pressed between aluminum sheets at 170°–200° C. on a hot press for one minute. The polypropylene film is fire resistant.

EXAMPLE 43

A mixture is made of:

| polypropylene powder (Melt index 10) | 90 | pbw |
|---|---|---|
| α-tetrachloroethylene-bis[-poly (halocyclohexane)]-phosphate (Example 30) | 7 | pbw |
| tetrachloroethylene-α'-2,4,6-tribromophenol-K-phosphate (Example 28) | 3 | pbw |
| Cadmium-β-chloroethylvinylphosphate | 0.05% | pbw of PP |
| Tinuvin P | 0.01% | pbw of PP |

A sample is rolled between 110°–135° C. and pressed between aluminum sheets at 170° to 200° C. on a hot press for one minute. The polypropylene film is fire resistant.

EXAMPLE 44

A mixture is made of:

| | |
|---|---|
| polypropylene powder (Melt index 10) | 90 pbw |
| α-tetrachloroethylene-bis[-α'-poly(halocyclohexane)]-phosphate (Example 30) | 7 pbw |
| $ZnCl_2$.2DMF | 0.5 to 5 pbw |
| $Sb_2O_3$ | 2.7 pbw |

A sample is rolled between 100°–135° C. and pressed between aluminum sheets at 170° to 200° C. on a hot press for one minute. The polypropylene film is fire resistant.

EXAMPLE 45

A mixture is made of:

| | |
|---|---|
| Pliovic S-51*(a PVC resin supplied by Goodyear Rubber Co.) | 90 pbw |
| α-tetrachloroethylene-α'-2,4,6-tribromophenol-K-phosphate (Example 28) | 7 pbw |

A sample is rolled between 80°–125° C. and pressed between aluminum sheets at 120° C. for 15–25 minutes. The PVC is dyeable and fire resistant.

*(The example could be repeated in presence of ETHYL Co. PVC resin SM-250)

EXAMPLE 46

A polyester panel is made by mixing the following ingredients and pressing them (hot).

| | |
|---|---|
| Hetron 23925 (polyester supplied by Hooker Chemical Co.) | 90 pbw |
| α-tetrachloroethylene-α'-2,4,6-tribromophenoxy-β-α-hydroxy-ethyl-metha-acrylate(Deriv. Example 29) | 8 pbw |

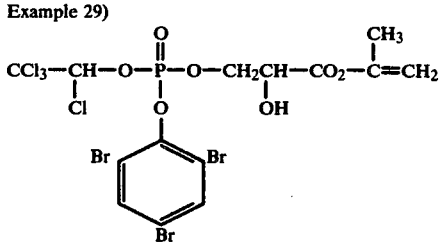

| | |
|---|---|
| Benzoylperoxide | 1.2% pbw of resin |
| $Sb_2O_3$ | 1.68 pbw |

The process is similar to Example 45 resulting in a fire resistant and dyeable product.

EXAMPLE 47

A polyester panel is made by mixing the following ingredients and pressing them (hot).

| | |
|---|---|
| Unsaturated polyester as described in USP 3,372,176 (by Diamond Shamrock Co.) | 90 pbw |
| bis(2,3,-dibromo-2-propene-1-oxy-βββ-tribromoethylene-α-oxy-phosphate-bis(β-chloromethyl-propane glycol (Example 24) | 5 pbw |
| $ZnCl_2$.2 DMF | 0.5 to 2 pbw |
| benzoylperoxyde | 1.06% pbw of resin |

The process is similar to Example 45 resulting in a dyeable and fire resistant product.

EXAMPLE 48

A polyester panel is made by mixing the following ingredients and pressing them (hot).

| | |
|---|---|
| PBT VERSEL-1200 (polyester by Allied Chem. Co.) | 90 pbw |
| O-ethyl-bis(α-oxy-α-40-hydroxy-ethyl-βββ-trichloro)-phosphate (Example 4) | 8 pbw |
| Zn $Cl_2$.2DMF | 0.5 to 5 pbw |
| $Sb_2O_3$ | 1.5 pbw |

The process is similar to Example 45 resulting in a fire resistant product.

EXAMPLE 49

A polyester panel is made by mixing:

| | |
|---|---|
| PBT-VERSEL-1100 (Polyester by Allied Chem. Co.) | 90 pbw |
| αtetrachloroethylene-β-chloro-propionamide-phosphorochloridate (As in Example 22) | 8 pbw |
| $SbCl_3$ DMF (or $ZnCl_2$2DMF) | 2 pbw |

The ingredients are mixed and pressed (hot) according to the condition described in Example 45 resulting in a fire resistant and dyeable product.

EXAMPLE 50

Polyurethane foam was prepared using methods, known to those skilled in the art, by reacting the following compounds:

Starch glucoside polyalkylene ether (with-OH 450 to 560) 8.89 g is blended with 4.40 g of bis(βββ-trichloro-α-hydroxyethylene) β'-oxy-diethyleneglycol-2-tetra-chloroethylene phosphate (as in Example 19) and 8.89 g toluene diisocyanate [or 50 to 70% (TDI blended with bis(βββ-trihalo-α-urylene-phenylisocyanate-β'-oxy-diethyleneglycol-tetrachloro ethylene phosphate) as in Example 27)] and heated 110 minutes. A non ionic vegetable oil emulsifier (0.50 g) and 0.5 g $H_2O$ containing 0.17 g triethylene diamine are added slowly with stirring 20 to 30 sec. The reaction mixture is poured into a waxed box for foam at room temperature to give a fire resistant polyurethane foam.

EXAMPLE 51

The procedure is similar to Example 50 where 2.00 g tetrachloro-ethylene-phosphate-bis(methoxy isocynate) are used as in Example 7 and 6.8 g silicon tetra-(methoxy-isocyanate)- in place of 8.89 g of TDI. The resulting foam is UV and fire resistant.

EXAMPLE 52

In the following examples is employed the formula (A):

| | |
|---|---|
| N-ethylmorpholine | 0.12 pbw |
| Silicone oil (Dow-Corning-50) | 0.03 pbw |

| -continued | |
|---|---|
| Dibutyltin | 0.08 pbw |
| Water | 0.46 pbw |

Polyol as in Example 32 such as bis($\beta\beta\beta$-tribromo-α-hydroxyethylene)-oxy-ethane-amino-ethoxy-2-bis(tetrabromopropane)-phosphate, 139 pbw is mixed with 8.89 pbw of polypropylene glycol. Upon addition of 3.33 g -bis($\beta\beta\beta$-trihaloethylene-α-urylene-phenyl isocyanate)-oxy-diethyleneglycol-2-tetrachloro ethylene-phosphate, (as in Example 27), 4,57 g of toluene diisocyanate is added. The resulting polyurethane foam is fire resistant.

EXAMPLE 53

A solid wood such as Douglass fir or chips, redwood, white fir, western hemlock, western pine, southern pine species of lumber, lawn-faced Douglass fir, southern pine plywood or carton is used. A ⅛" screen is impregnated with $\beta\beta\beta$-trichloro-α-hydroxy ethyl-β-ethoxyphosphonate (Example 1) or O,O-dimethyl-bis (α-oxy-α'-hydroxyethyl-$\beta\beta\beta$-trichloro)-phosphonate (As Example 3) 70 to 80% pbw, tris(haloaliphatic)-phosphites such as tri-(β-chloropropyl)-phosphite 30 to 20% pbw which are diluted with methylenechloride or chloroethylene derivatives with bp.less than 100° C. at 15 to 70% pbw of the materials. At the room temperature the materials are impregnated between 2.5 to 50 atm. for 80 to 100 minutes and then under the heat the solvent is removed resulting in fire resistant wood, chips, or carton without alteration of physical properties, and with moisture resistance.

That which is claimed is:

1. A compound having the formula selected from the group consisting of

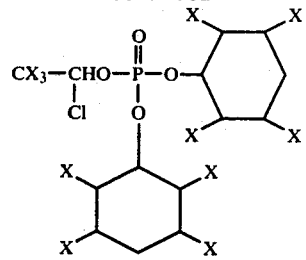

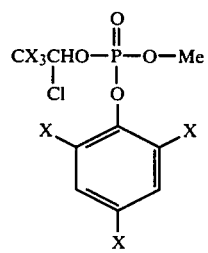

and

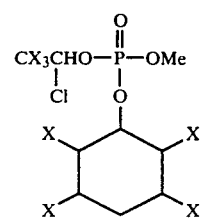

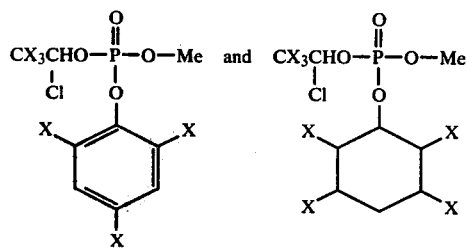

where
X=Cl, Br
Me=Na, K, Li, Zn, Mg, Ni, Ca, Ba, Sb, Ti, V, Sn or H.

2. A compound having the formula selected from the group consisting of

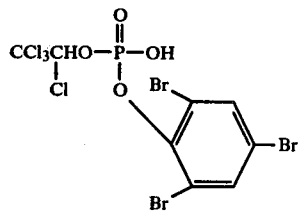

where
X=Cl or Br
Me=Na, K, Li, Zn, Mg, Ni, Ca, Ba, Sb, Ti, V, Sn or H.

3. A compound having the formula

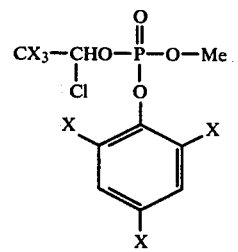

4. A compound having the formula where
X=Cl or Br
Me=Na, K, Li, Zn, Mg, Zn, Ca, Ba, Sb, Ti, V, Sn or H.

* * * * *